United States Patent [19]

Stuebner

[11] Patent Number: 4,580,408

[45] Date of Patent: Apr. 8, 1986

[54] WATER VEST FOR MOTOCROSS RIDERS

[76] Inventor: Patricia A. Stuebner, 141 E. Hillcrest Blvd., Monrovia, Calif. 91016

[21] Appl. No.: 588,675

[22] Filed: Mar. 12, 1984

[51] Int. Cl.$^4$ ............................................. A61F 7/00
[52] U.S. Cl. ........................................ 62/259.3; 2/2.5; 2/81; 2/92; 2/DIG. 1; 128/400; 128/402
[58] Field of Search ...................... 128/400, 402, 403; 62/259.3; 2/92, 102, DIG. 1, 2

[56] References Cited

U.S. PATENT DOCUMENTS

| | | | |
|---|---|---|---|
| 2,756,746 | 7/1956 | Munrett | 128/165 X |
| 2,875,447 | 3/1959 | Goldmerstein | 62/259.3 X |
| 3,125,865 | 3/1964 | Bemelman | 128/400 X |
| 3,135,961 | 6/1964 | Roderick | 2/92 X |
| 3,610,323 | 10/1971 | Troyer | 128/402 X |
| 3,861,389 | 1/1975 | Winther | 128/403 |
| 3,950,789 | 4/1976 | Konz et al. | 128/402 X |
| 4,033,354 | 7/1977 | De Rosa | 128/402 X |

Primary Examiner—Anton O. Oechsle
Attorney, Agent, or Firm—Christie, Parker & Hale

[57] ABSTRACT

A water vest for motocross riders comprises a combination of shoulder pads for the motocross rider, and a water absorbing and air cooling layer attached to the inside of the shoulder pads for overlying the chest area of the motocross rider. The shoulder pads are in the shape of a vest having a front face for overlying the chest area of the rider. The front face is perforated so it is porous to air. The water absorbing and air cooling layer includes an elongated jacket having flexible outer plies porous to air and water. A water absorbing layer, preferably multiple thin layers of a water absorbing material, are disposed in the hollow interior of the jacket. The water absorbing material is capable of absorbing many times its weight in water and is porous to traveling air when water is retained by it. Fasteners removably attach the water absorbing and cooling layer to the front face of the shoulder pads. The water absorbing layer is soaked in water and then fastened to the inside of the shoulder pads. The absorbed water provides cooling for traveling air passing through the rider's clothing, through the front of the shoulder pads, and through the water retained in the water absorbing layer to allow the air to circulate through to the chest region of the rider which thereby reduces heat exhaustion and fatigue during racing, particularly in hot weather.

18 Claims, 5 Drawing Figures

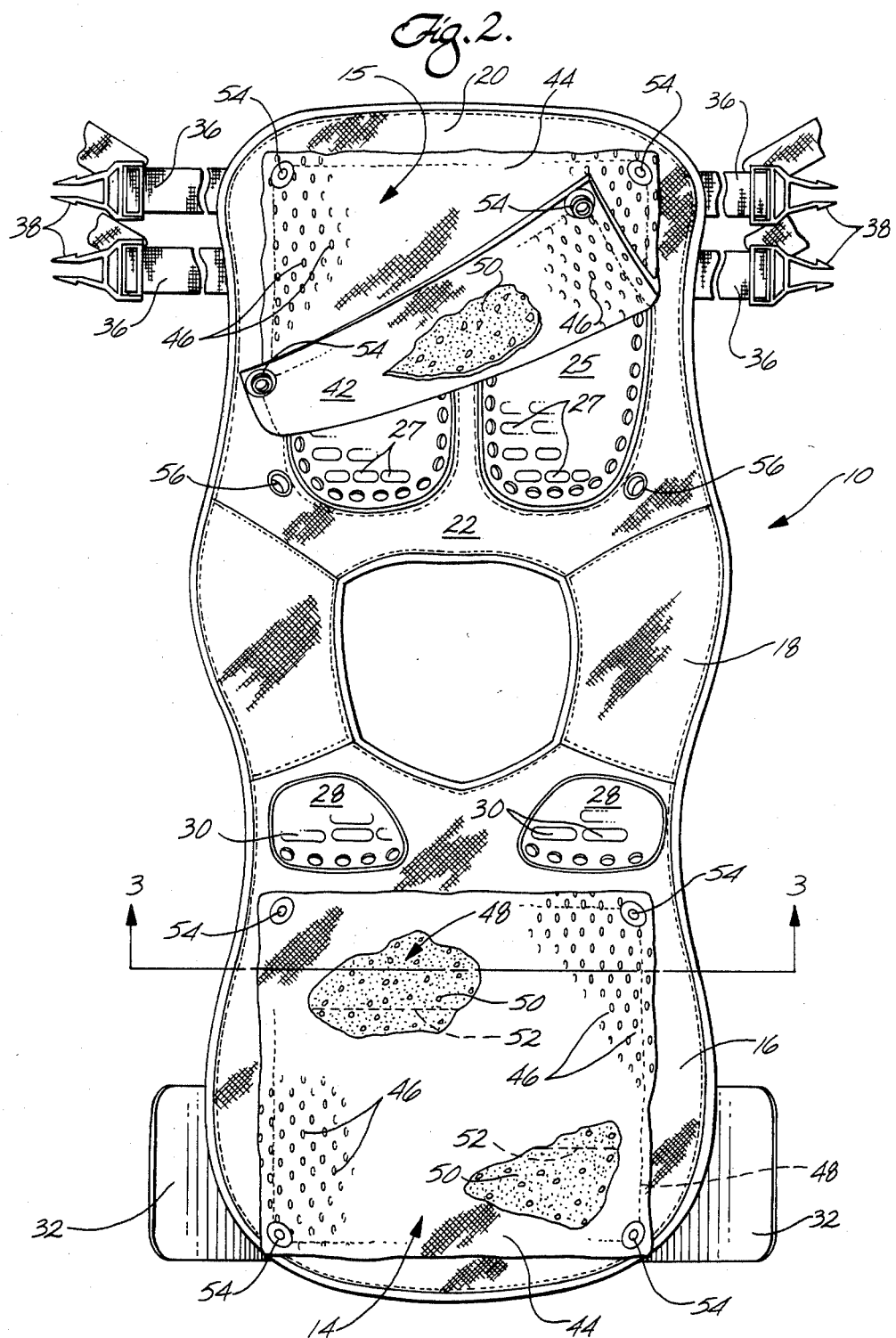

WATER VEST FOR MOTOCROSS RIDERS

FIELD OF THE INVENTION

This invention relates to a water vest worn by motocross riders to alleviate heat exhaustion or fatigue when racing in hot weather.

BACKGROUND OF THE INVENTION

Motocross riders often experience undue fatigue or heat exhaustion when racing in hot weather. Many races are held in a desert where hot weather prevails, so overheating is a common problem for many motocross racers. The tight closed course over terrain that includes steep hills, sharp turns and other hazards adds to the problem.

It is common for motocross racers to wear an outer riding shirt and protective gear such as a chest protector and shoulder pads under the riding shirt. The problem of overheating is magnified because such protective equipment adds weight and inhibits dissipation of body heat that builds up as the race progresses, particularly in hot weather.

The present invention provides a water vest that reduces heat exhaustion and fatigue of a motocross racer in hot weather. The water vest provides a means for cooling air that passes to the skin of the rider and thereby keeps the rider cool over a longer period of time during a race. The water vest can keep a motocross rider cool for about 30 to 40 minutes of racing on a hot day with temperatures in the 85° to 100° F. range. The water vest also is easy and convenient to use and it adds little weight to the riding equipment.

SUMMARY OF THE INVENTION

Briefly, one embodiment of the water vest comprises the combination of shoulder pads that provide protective equipment for a motocross rider, and a water absorbing layer attached to the inside of the shoulder pads for retaining water and providing cooling for the chest area of the motocross rider when racing. The shoulder pads are in the general shape of a vest having a front face for overlying the front of the upper torso of the rider. Shoulder support means extend over the shoulders of the rider for supporting the front face of the shoulder pads so it overlies the chest area of the rider. The front face of the shoulder pads is perforated so that it is porous to air. The water absorbing layer includes an elongated jacket having outer plies surrounding a hollow interior that contains a layer of water absorbing material. The outer plies of the jacket are porous to air and water, and the jacket is of a size and shape to overlie a substantial area of the front face of the shoulder pads. The layer of water absorbing material is in panel form and extends over a substantial area of the jacket interior. The water absorbing material is capable of absorbing many times its weight in water and is porous to traveling air. Water retained by it cools the traveling air. Fasteners on the jacket and on the front face of the shoulder pads provide means for removably fastening the jacket and its water absorbing layer to the inside of the shoulder pads. The jacket can be removed from the shoulder pads, soaked in water, and then fastened to the inside of the shoulder pads. Water retained by the water absorbing layer provides cooling for traveling air passing through the shoulder pads, the jacket, and the water absorbing layer, so that the body of the rider is cooled during use. The water absorbing layer retains sufficient water the cooling can be achieved over a prolonged period of time.

In another embodiment, the water absorbing layer is adapted for use with a racing shirt also used by motocross racers.

In either embodiment, the water absorbing layer and the jacket material, as well as the garmet to which they are attached allow for good circulation of cooling air through the water soaked layer to the skin so that, during racing, the traveling air which is constantly present can be cooled and used as a means for cooling down the rider.

Other advantages are also described with respect to the following detailed description and the accompanying drawings.

DRAWINGS

FIG. 2 is a fragmentary elevation view, partly broken away, showing the inside face of the water vest in flat form.

DETAILED DESCRIPTION

Figure 1:
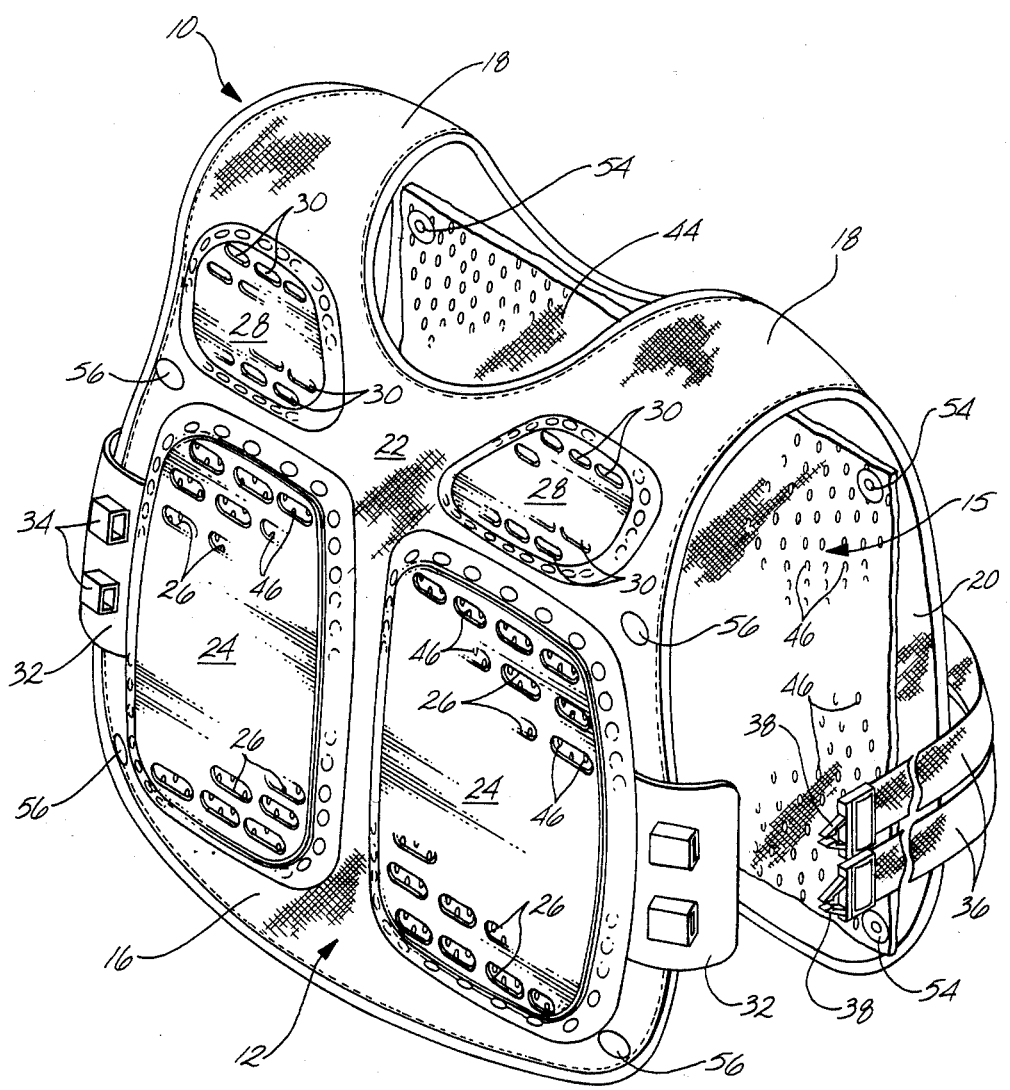
FIG. 1 is a perspective view showing a water vest for motocross riders according to principles of this invention.

FIGS. 1 and 2 are a perspective view and an elevation view showing a water vest 10 according to principles of this invention. The water vest is used by motocross riders who commonly have a problem with heat exhaustion in the summer, particularly when racing in the desert. The water vest is worn to provide cooling, particularly taking advantage of traveling air during a race to cool the air and allow it to circulate to the skin so that the motorcross racer can remain cool for a long period of time. In the embodiment of FIGS. 1 and 2, the water vest comprises a combination of shoulder pads 12 commonly used by motocross racers as protective equipment together with front and rear water absorbing and cooling layers 14 and 15, respectively, attached to inside faces of the shoulder pads. The shoulder pads actually are a combination of a chest and back protector in addition to shoulder pads, but they are referred to as "shoulder pads" for simplicity. In the embodiment of FIG. 1, the shoulder pads have a front chest protector 16 for overlying the chest region of the rider, a pair of shoulder straps 18 or shoulder supports that extend over the shoulders of the rider, and a back protector 20 that extends over the rider's back.

The shoulder pads are made principally from a rugged flexible piece 22 of fabric such a woven nylon, polyester or cotton. The chest protector 16 of the shoulder pads comprises the flexible piece 22 that overlies substantially the entire area of the rider's upper torso. This is reinforced with chest protective means which are preforated in some manner to allow air to pass through for ventilation. In the illustrated embodiment, the chest protector has two side-by-side chest protective sections 24 made from a material with more rigidity than the flexible fabric 22 to which they are attached. These chest protective sections are preferably made of a semi-rigid plastic material such as polypropylene, and each chest protective section has spaced part rows of large vent holes 26 which are reasonably large to allow a substantial amount of traveling air to pass through them during use. A pair of upper protective sections 28 are also carried by the chest protector. Each of these upper protective sections is located above a respective one of the chest protective sections for overlying the right and left collarbone regions of the rider. Each of the upper protective sections 28 is made from a semi-rigid plastic material similar to the chest protective sections 24, and each upper protective section has simiilar large vent holes 30 for allowing a substantial amount of air to pass through those regions of the chest protector.

The shoulder pads also include semi-rigid back protective sections 25, (see FIG. 2) carried by the flexible back protector 20. The back protective sections have large vent holes 27.

The shoulder panels are used by placing the shoulder strap regions 18 of the shoulder pads over the rider's shoulders so the chest protector 16 and the back protector 20 overlie the rider's chest and back. The chest and back protectors are sufficiently wide to cover most of the area of the rider's chest and back. Opposite side edges of the chest protector have flexible flaps 32 each of which carries a pair of tubular open-ended locks 34. A separate pair of adjustable waist straps 36 are secured to and extend laterally away from opposite sides of the back protector. Each of these straps has a separate spring biased catch 38 adapted to slide into a corresponding lock 34 and be released from its locked position and slid out of contact with the lock. Thus, once the shoulder pads are in place supported on the shoulders and overlying the chest and back regions of the rider, the waist belts on both sides can be snap locked to hold the shoulder pads in place firmly on the rider's upper torso to prevent twisting or other undesired movement or slipping of the shoulder pads.

According to principles of this invention, the shoulder pads are worn in combination with the front water absorbing and cooling layer 14 which releasably attaches to the inside face of the chest protector 16 of the shoulder pads. The water absorbing and cooling panel includes an outer jacket made from inner and outer plies 42 and 44 of a flexible fabric. In the illustrated embodiment, the jacket is generally rectangular in shape, and the inner and outer plies of the jacket overlie one another and are fastened together around their periphery by stitching, or at least folded over so that the outer jacket is closed along three sides or four sides to form a hollow interior or enclosure. The jacket layers are preferably made from a perforated material that is porous to air and water and is also capable of absorbing reasonable amount of water. Preferred materials are fabrics made from woven fibers of nylon, polyester, or cotton. In the illustrated embodiment, rows of spaced apart perforations 46 are spread across the entire surface of each ply of the jacket material. It is important that the jacket material allow water to pass freely through it to the interior of the jacket. It also allows traveling air to pass freely through it during use.

The water absorbing and cooling layer 14 also includes a water absorbing material 48 disposed within the hollow interior of outer jacket. The water absorbing material is in flat layer form and is made from a material capable of absorbing several times its weight in water. It is also porous to traveling air when the water is absorbed and retained by the material. Preferred materials are flexible, resilient, self-supporting water absorbing materials such as sponge, sponge rubber, or polyurethane foam. The water absorbing material preferably is about the same size and shape as the outer jacket so it fills the interior of the jacket.

Figure 3:
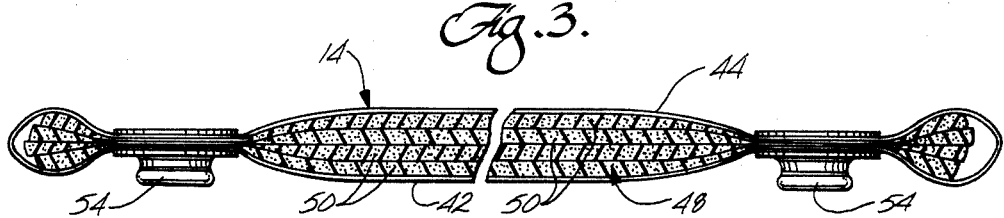
FIG. 3 is a fragmentary cross-sectional view taken on line 3—3 of FIG. 2.

FIG. 3 illustrates a preferred means for arranging the water absorbing material as several thin layers 50 overlying one another and in surface contact with one another. In the illustrated embodiment, there are preferably four thin layers each about ¼-inch thick, although more or fewer thin layers can be used. The layers are each single layers continuous with the interior surface area of the outer jacket.

Figure 4:
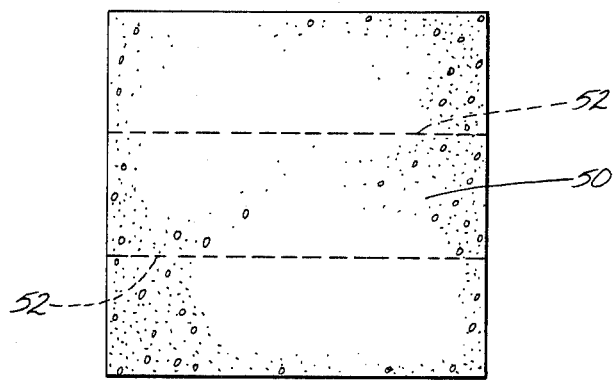
FIG. 4 is an elevation view showing one embodiment of a water absorbing layer used with the water vest.

FIG. 4 illustrates an embodiment in which the multiple layers 50 of water absorbing material are stitched together at vertically spaced apart, horizontally extending intervals, preferably by rows of stitching 52. One such row of stitching or several rows can be used.

The front water absorbing and cooling layer 14 is removably fastened to the inside face of the chest protector 16. Preferably it is fastened by snap ring fasteners 54 secured near the four corners of the jacket 44 and by cooperating snap ring fasteners 56 secured to the chest protector. Other similar fasteners such as Velcro fasteners can be used.

The shoulder pads shown in FIGS. 1 and 2 also are adapted to hold the rear water absorbing and cooling layer 15 attached to the inside face of the back protector 20. This layer is optional in that a majority of the cooling effect of this invention is provided by the front layer 14. However, the rear layer 15 provides an additional useful amount of cooling and therefore its preferred. In the illustrated embodiment, the rear layer 15 is identical to the front layer 14 and thus includes the multiple thin flexible layers 50 of water absorbing material inside an outer jacket having the inner and outer plies 42 and 44 of fabric with perforations 46 for allowing passage of air and water to the water absorbing layer. The rear layer 15 also includes the snap ring fasteners 54 and its corners for attachment to the cooperating snap ring fasteners 56 affixed to the back protector 20.

Figure 5:
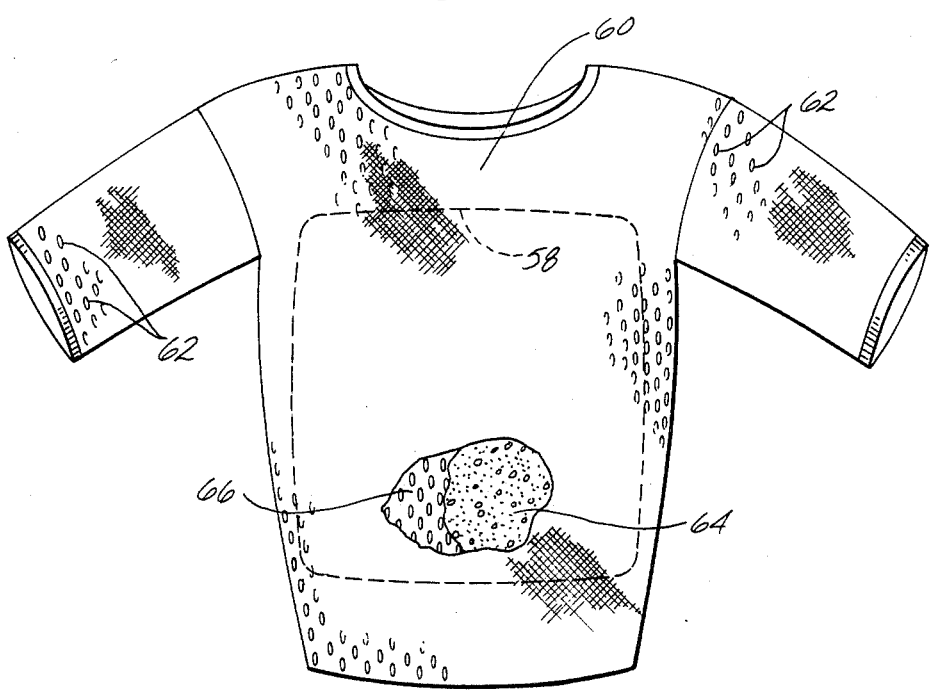
FIG. 5 is an elevation view, partly broken away, showing an alternate embodiment of the water vest.

FIG. 5 shows an alternate embodiment of the invention in which a water absorbing and air cooling layer 58 similar to layers 14 and 15 described above is worn on the inside front face of a riding shirt 60. The riding shirt is made from a flexible material having perforations 62 spread over the entire face of the shirt to provide air ventilation. It is also porous to water. The water absorbing layer is preferably sewn into the inside of the shirt. The layer 58 preferably includes the multiple and inner layers 64 of the water absorbing material and an outer ply 66 of a flexible porous material on a side of the layers 64 opposite from the front of the shirt. The outer play is sewn to the shirt and combines with the shirt to form a hollow interior for holding the water absorbing layers 64.

In using the water vest (of FIGS. 1–4), the motocross rider prior to the race removes the water absorbing layers from the inside of the chest and back protectors and then soaks the water absorbing layers in water. The interior layers of water absorbing material absorb several times their weight in water. The water saturated layers are then fastened to the inside faces of the chest and back protectors. The water vest is put on under the rider's shirt so that the water saturated layers are next to the skin. The rider then puts on a riding shirt over the shoulder pads. The riding shirt is perforated so that it breathes and therefore allows air to pass through it. The vent holes in the protective sections of the chest protector also allow air to pass through to the water absorbing layer. The water retained by the water absorbing layer produces a cooling effect from the wind that passes through the vest to the water absorbing layers during a race. As the water evaporates from the water absorbing layers it cools the passing air which circulates to the chest region of the rider and reduces body heat. The multiple interior water absorbing layers have been found to retain sufficient water to provide effective cooling for up to 30 to 40 minutes while racing in hot weather where ambient temperatures ae in the range of 85° to 100° F.

The separate water absorbing layers also enhance circulation of traveling air through the water absorbing layer and improve the transfer of cooling from the water to the traveling air. Air passes through the thin layers, and the thin layers form air pockets between them which tends to retain water that provides effective cooling for the air traveling through them. It has been found that the cooling effect of this invention is not produced as significantly by a single layer of the same water absorbing material of the same total thickness as the multiple layers. It has also been found that the rows of stitching on the multiple layers provide an improved means of retaining water by the water absorbing layer, as opposed to overlying water absorbing layers that are not fastened together. It has been found that the rows of stitching reduce rapid drainage of water to the bottom of the jacket. Therfore, the water is retained at different elevations in the water absorbing layer so that the water is more uniformly present throughout the layer to provide its cooling effect. In contrast, a single layer or multiple layers that are not fastened together tend to allow the water to drain to the bottom of the jacket under gravity more rapidly and thereby reduce the long term cooling effect.

In using the embodiment of FIG. 5, the racing shirt itself is simply soaked in water before the race. The shirt material and the inside ply 66 allow water to pass through to the inside layers 64 of water absorbing material. The shirt ply and the inside ply 66 also provide a means for retaining water in the water absorbing layers to enhance the long term cooling effect.

I claim:

1. A water vest for motocross racers comprising the combination of:
   protective shoulder pads for motocross racing in the shape of a vest having a front face for overlying the front of the upper torso of a motocross rider, impact-protective means on the front face of the shoulder pads, and shoulder support means for extending from the front face of the shoulder pads over the shoulders of the rider for holding the front face of the shoulder pads over the upper torso, said front face being perforated so it is porous to air;
   an elongated jacket having flexible outer plies surrounding a hollow interior, the flexible outer plies of the jacket being porous to air and water, the jacket having a size and shape to overlie a substantial area inside the front face of the shoulder pads;
   a water-absorbing layer of a flexible, resilient, sponglike material in self-supporting panel form disposed within and extending over a substantial area of the hollow interior of the flexible jacket, the water-absorbing material being capable of holding several times its weight in water and being porous to traveling air when water is absorbed and retained by it; and
   fastening means for removably fastening the jacket and its water-absorbing layer to the inside of the front face of the shoulder pads so that the jacket can be removed from the front face of the shoulder pads, soaked in water to absorb water into the water-absorbing material, and then fastened to the inside of the front face of the shoulder pads, the water-absorbing layer providing cooling from traveling air passing through the perforated front face of the shoulder pads, the jacket, and the water-absorbing layer to the body of the rider wearing the water vest.

2. Apparatus according to claim 1 in which the water absorbing layer comprises multiple thin layers of the water absorbing material in flat form disposed adjacent one another and in surface contact with one another.

3. Another according to claim 2 including one or more means for securing the layers together across a horizontally extending interface to enhance water retention by the multiple layers.

4. Apparatus according to claim 2 in which the sponge-like material is selected from the group consisting of sponge, sponge rubber, or a resilient plastic foam material.

5. Apparatus according to claim 2 in which the impact-protective means on the shoulder pads comprise one or more impact-protective sections having a rigidity greater than a remaining portion of the front face of the shoulder pads; and in which the perforations on the front face of the shoulder pads include vent holes in said rigid impact-protective sections.

6. Apparatus according to claim 1 including one or more rows of stitching extending horizontally across the water-absorbing layer to provide an interface to enhance water retention by the water-absorbing layer.

7. Apparatus according to claim 1 in which the sponge-like material is selected from the group consisting of sponge, sponge rubber, or a resilient plastic foam material.

8. Apparatus according to claim 1 in which the impact-protective means on the shoulder pads comprise one or more impact-protective sections have a rigidity greater than a remaining portion of the front face of the shoulder pads; and in which the perforations on the front face of the shoulder pads include vent holes in said rigid impact-protective sections.

9. A water vest for motocross racers comprising the combination of:
   a riding shirt having at least a front face for overlying the front of the upper torso of a motocross rider, the front face of the riding shirt being perforated so it is porous to air and water;
   a water-absorbing layer of a flexible, resilient, sponge-like material in self-supporting panel form overlying the inside surface of the front face of the riding shirt so that the water-absorbing layer extends over a substantial area of the riding shirt, the water-absorbing material being capable of holding several times its weight in water and being porous to traveling air when water is absorbed and retained by it, the water-absorbing layer comprising multiple thin layers of the sponge-like water-absorbing material in flat form disposed in surface contact with one another;
   a flexible outer ply of a material that is porous to air and water overlying the water-absorbing layer on a side thereof opposite from the front face of the riding shirt; and means securing the outer ply to the front face of the riding shirt to hold the water-absorbing layer in place adjacent the inside surface of the riding shirt front face and adjacent the outer ply of porous material so that the shirt can be soaked in water to transfer water through the front face of the shirt and through the outer ply into the water-absorbing layer so that the shirt when worn can allow traveling air to pass through the perforated front face of the shirt and through the water retained in the water-absorbing layer and through the perforated outer ply to the skin of the rider wearing the shirt, with the multiple sponge-like water-absorbing layers forming air pockets between them for enhanced cooling of the traveling air.

10. Apparatus according to claim 9 in which the front face of the riding shirt includes large perforations separate and apart from the material from which the shirt is made so that the front face of the shirt is porous to air and water.

11. Apparatus according to claim 10 including one or more means for securing the multiple layers of water-absorbing material together across a horizontally extending interface to enhance water retention of the multiple layers.

12. Apparatus according to claim 9 including one or more means for securing the multiple layers of water-absorbing material together across a horizontally extending interface to enhance water retention of the multiple layers.

13. A water vest for motocross racers comprising the combination of:

protective shoulder pads for motocross racing in the shape of a vest having a front face for overlying the front of the upper torso of a motocross rider, impact-protective means on the front face of the shoulder pads, the front face of the shoulder pads having perforations so it is porous to traveling air, and shoulder support means for extending from the front face of the shoulder pads over the shoulders of the rider for holding said front face over the upper torso of the rider;

an elongated jacket having flexible outer plies surrounding a hollow interior, the flexible outer plies of the jacket being porous to air and water, the jacket having a size and shape to overlie a substantial area inside the front face of the shoulder pads;

a water-absorbing layer of a flexible, resilient, sponge-like material in self-supporting panel form disposed within and extending over a substantial area of the hollow interior of the flexible jacket, the water-absorbing material being capable of holding several times its weight in water and being porous to traveling air when water is absorbed and retained by it; and means for independently positioning the jacket and its water-absorbing layer relative to the inside of the front face of the shoulder pads so that the jacket can be removed from the front face of the shoulder pads, soaked in water to absorb water into the water-absorbing material, and then positioned adjacent the inside of the front face of the shoulder pads so that the water-absorbing layer provides cooling from traveling air passing through the perforated front face of the shoulder pads, the jacket, and the water-absorbing layer to the body of the rider wearing the water vest.

14. Apparatus according to claim 13 in which the water-absorbing layer comprises multiple thin layers of the water-absorbing material in flat form disposed and in surface contact with one another.

15. Apparatus according to claim 14 including one or more means for securing the multiple water-absorbing layers together across a horizontally extending interface to enhance water retention by the multiple layers.

16. Apparatus according to claim 14 in which the sponge-like material is selected from the group consisting of sponge, sponge rubber, or a resilient plastic foam material.

17. Apparatus according to claim 16 in which the impact-protective means on the shoulder pads comprise one or more impact-protective sections having a rigidity greater than a remaining portion of the front face of the shoulder pads; and in which the perforatiions on the front face of the shoulder pads include vent holes in said rigid impact protective sections.

18. Apparatus according to claim 13 in which the impact-protective means on the shoulder pads comprise one or more impact-protective sections having a rigidity greater than a remaining portion of the front face of the shoulder pads; and in which the perforations on the front face of the shoulder pads include vent holes in said rigid impact protective sections.

* * * * *